(12) United States Patent
Salvatore (10) Patent No.: US 9,581,542 B2
(45) Date of Patent: Feb. 28, 2017

(54) DEVICE FOR DETECTING THE CONCENTRATION OF A SOLUTION

(71) Applicant: SIGMAR S.R.L., Ozegna (Turin) (IT)

(72) Inventor: Osvaldo Salvatore, Ozegna (IT)

(73) Assignee: LITTELFUSE ITALY S.R.L, Milan (MI) (IT)

( * ) Notice: Subject to any disclaimer, the term of this patent is extended or adjusted under 35 U.S.C. 154(b) by 0 days.

(21) Appl. No.: 14/661,943

(22) Filed: Mar. 18, 2015

(65) Prior Publication Data

US 2016/0084754 A1 Mar. 24, 2016

(30) Foreign Application Priority Data

Sep. 24, 2014 (EP) ..................................... 14186120

(51) Int. Cl.
*G01N 21/00* (2006.01)
*G01N 21/27* (2006.01)
(Continued)

(52) U.S. Cl.
CPC .......... *G01N 21/27* (2013.01); *G01N 21/255* (2013.01); *G01N 21/431* (2013.01); *G01N 21/59* (2013.01); *F01N 2610/02* (2013.01); *F01N 2900/1806* (2013.01); *G01N 21/8507* (2013.01); *G01N 2021/432* (2013.01); *G01N 2201/0621* (2013.01); *G01N 2201/0627* (2013.01)

(58) Field of Classification Search
CPC ...... G01N 21/27; G01N 21/255; G01N 21/59; G01N 2201/0621; G01N 21/431; G01N 21/05; G01N 21/31; B01D 53/30

USPC .................. 356/442, 437, 445, 338–339, 320
See application file for complete search history.

(56) References Cited

U.S. PATENT DOCUMENTS 3,917,410 A 11/1975 Ulrich
3,995,169 A * 11/1976 Oddon ................ G01F 23/2927
250/577

(Continued)

FOREIGN PATENT DOCUMENTS

EP 2067517 A2 6/2009
EP 2067517 A3 11/2011
JP 2001020724 A 1/2001

OTHER PUBLICATIONS

European Search Report dated Apr. 8, 2015, and completed on Mar. 24, 2015, from corresponding Application No. 14186120.3.
(Continued)

*Primary Examiner* — Tarifur Chowdhury
*Assistant Examiner* — Isiaka Akanbi (57) ABSTRACT

A device for detecting the concentration of a given component in a solution, preferably the concentration of urea in solution with water includes a means for emitting radiation, at least one means for receiving radiation, which is prearranged for determining at least one characteristic of the radiation, and a light guide, which is prearranged for optically connecting the emitting means to the receiving means, wherein the light guide has at least one surface that is to come into contact with the solution so as to determine an interface of separation between the propagation medium and the solution. Control means are configured for obtaining a value indicating the concentration of the compound in the solution as a function of the signal coming from the receiving means.

13 Claims, 6 Drawing Sheets

(51) Int. Cl.
*G01N 21/59* (2006.01)
*G01N 21/25* (2006.01)
*G01N 21/43* (2006.01)
*G01N 21/85* (2006.01)

(56) References Cited

U.S. PATENT DOCUMENTS

| | | | | |
|---|---|---|---|---|
| 4,082,959 | A * | 4/1978 | Nakashima | G01F 23/2925 250/577 |
| 4,287,427 | A * | 9/1981 | Scifres | G01N 21/431 250/577 |
| 4,806,013 | A | 2/1989 | Bodenheimer | |
| 4,834,533 | A * | 5/1989 | Horike | G01N 21/431 250/227.23 |
| 5,121,986 | A * | 6/1992 | Rutz | G01N 21/431 356/133 |
| 5,864,397 | A * | 1/1999 | Vo-Dinh | G01N 21/658 356/301 |
| 5,966,477 | A | 10/1999 | Johnson | |
| 8,570,520 | B2 * | 10/2013 | Fleischer | G01N 21/05 356/437 |
| 2006/0017930 | A1 * | 1/2006 | Canty | G01N 21/8507 356/436 |
| 2007/0079599 | A1 * | 4/2007 | Osaku | F01N 3/2066 60/283 |
| 2010/0025048 | A1 * | 2/2010 | Franzen | E21B 43/24 166/385 |
| 2012/0170044 | A1 * | 7/2012 | Prabhakar | G01N 21/05 356/440 |
| 2014/0132951 | A1 | 5/2014 | Georis | |

OTHER PUBLICATIONS

Mahalik, K et al, "Kinetic studies on hydrolysis of urea in a semi-batch reactor at atmospheric pressure for safe use of ammonia in a power plant for flue gas conditioning," Journal of Hazardous Materials, vol. 175, No. 1-3, Mar. 15, 2010, pp. 629-637.

* cited by examiner

DEVICE FOR DETECTING THE CONCENTRATION OF A SOLUTION

CROSS REFERENCE TO RELATED APPLICATIONS

This application claims priority from European patent application No. 14186120.3 filed on Sep. 24, 2014, the entire disclosure of which is incorporated by reference.

FIELD OF THE INVENTION

The present invention relates to a device for detecting the concentration of a solution, preferably the concentration of urea in solution with water.

BACKGROUND

As is known, in the art there exist devices designed to reduce emissions of nitrogen oxide that comprise a catalytic system in which, injected into a compartment traversed by the exhaust gases, is a solution of urea that is to dissociate thermally so as to liberate ammonia, which combines with the nitrogen oxides so as to reduce them and obtain free nitrogen and water. This catalytic system is referred to as selective catalytic reduction (SCR). The system in question carries out a control on the value of the concentration of urea in the solution of urea and water used in order to calibrate its own operating mode appropriately. In particular, as a function of the concentration value, the system varies the flow rate of solution injected into the reaction chamber. Furthermore, the system checks that the concentration value remains within a predetermined range so that proper operation of the system itself is guaranteed.

The foregoing imposes the need to install on the vehicle a sensor device designed to determine the concentration of urea in the solution.

In the technical field in question there is moreover felt the need to be able to verify on board the vehicle that the solution for the catalytic system mentioned above effectively contains urea. There has in fact been noted the risk of other liquids accidentally mixing with the solution in question, such as for example engine coolant or diesel. Coolant may, in the case of leakages in the coolant-circulation system, mix with the solution of water and urea within the reservoir that contains the solution, which is heated by the coolant during starting of the vehicle engine. Diesel, instead, may be introduced by mistake into the reservoir of the solution of urea and water in the cases where this is located adjacent to the diesel tank. Another cause of the presence of foreign liquids is represented by fraudulent actions whereby, instead of the solution of urea and water, liquids of some other type, whether surrogates or not, having a far lower cost are supplied.

OBJECT OF THE INVENTION

In the technical field in question, the object of the present invention is to provide a sensor device that will be able to meet one or more of the aforesaid requirements and that at the same time will present precise and reliable operation.

The above object is achieved thanks to a sensor device presenting the characteristics specified in the attached claims.

The claims form an integral part of the technical teaching provided herein in relation to the invention.

BRIEF DESCRIPTION OF THE DRAWINGS

Further characteristics and advantages of the invention will emerge clearly from the ensuing description with reference to the annexed drawings, which are provided purely by way of non-limiting example and in which.

DETAILED DESCRIPTION

In the ensuing description, various specific details are illustrated aimed at providing an in-depth understanding of the embodiments. The embodiments may be obtained without one or more of the specific details, or with other methods, components, or materials, etc. In other cases, known structures, materials, or operations are not illustrated or described in detail so that various aspects of the embodiment will not be obscured.

The references used herein are provided merely for reasons of convenience and hence do not define the sphere of protection or the scope of the embodiments.

The present invention relates to a device for detecting the concentration of a solution, preferably the concentration of urea in solution with water. Measurement of the concentration of urea in water constitutes the preferred application for which the present applicant has developed the new device in question. In any case, the present applicant has found that the device described herein can at any rate be used for measuring concentrations of other solutions, as will be discussed hereinafter.

Figure 2:
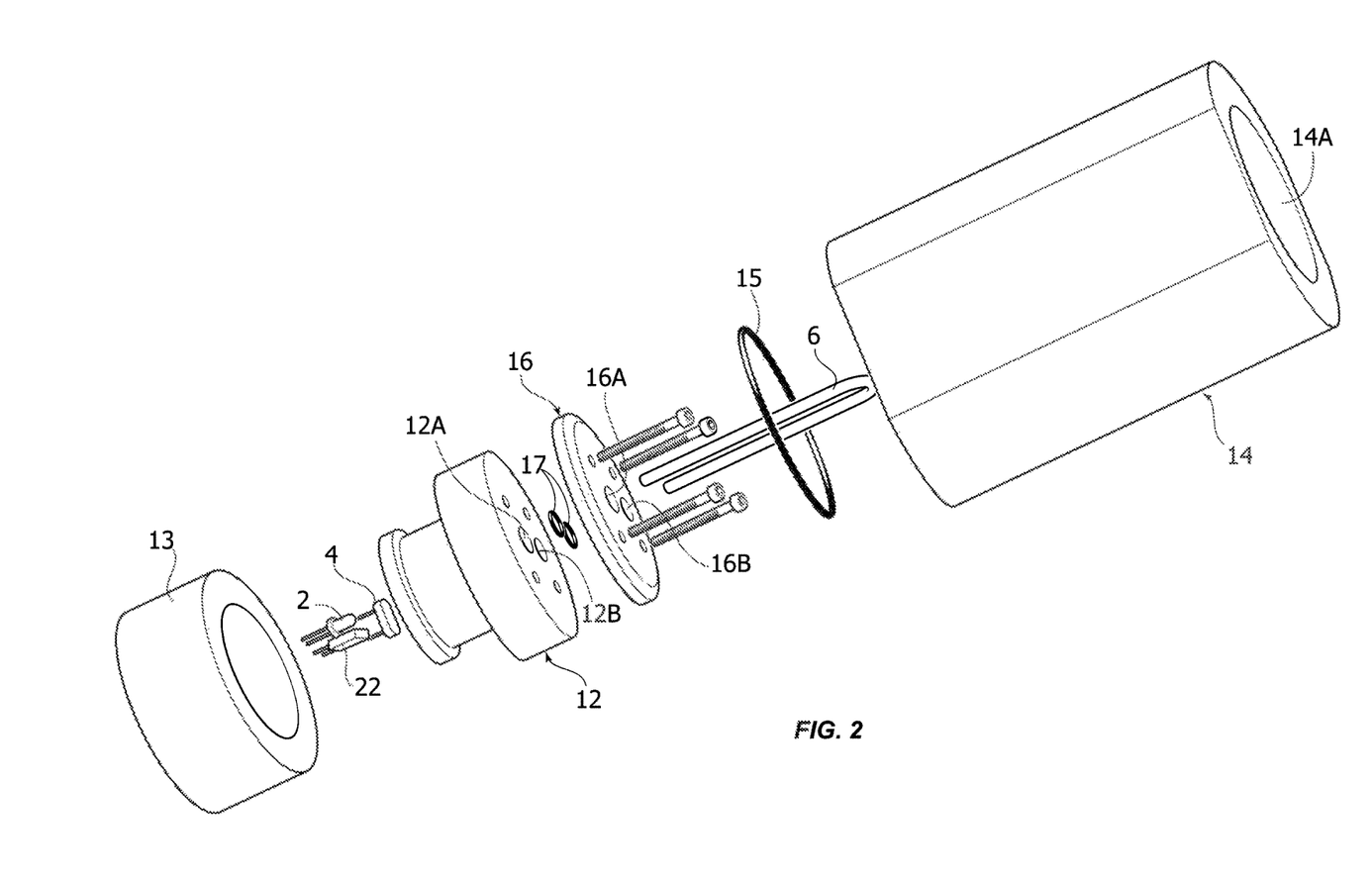
FIG. 2 is an exploded perspective view of the device of FIG. 1.
Figure 3:
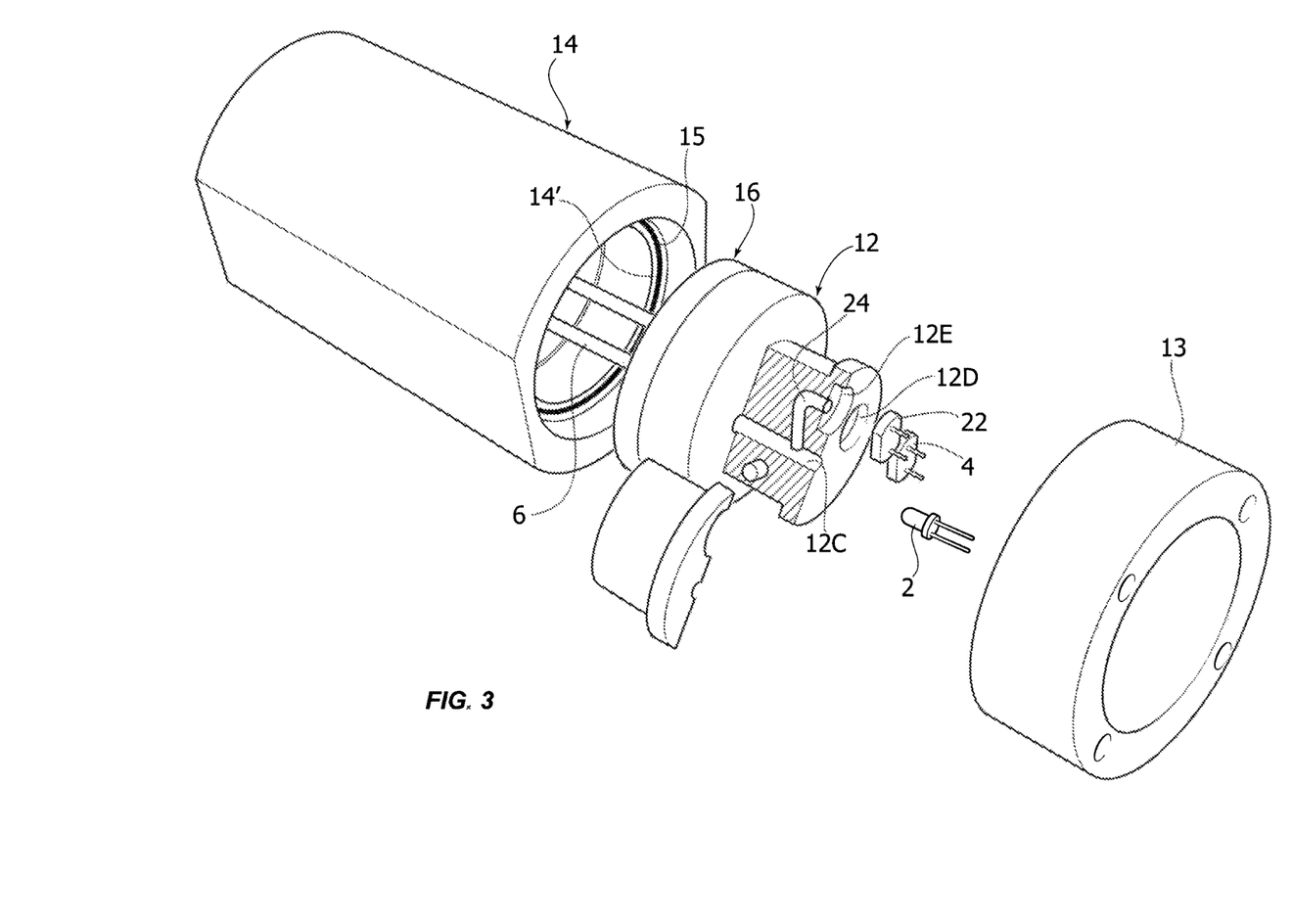
FIG. 3 is an exploded perspective view of a second embodiment of the sensor device described herein.
Figure 4:
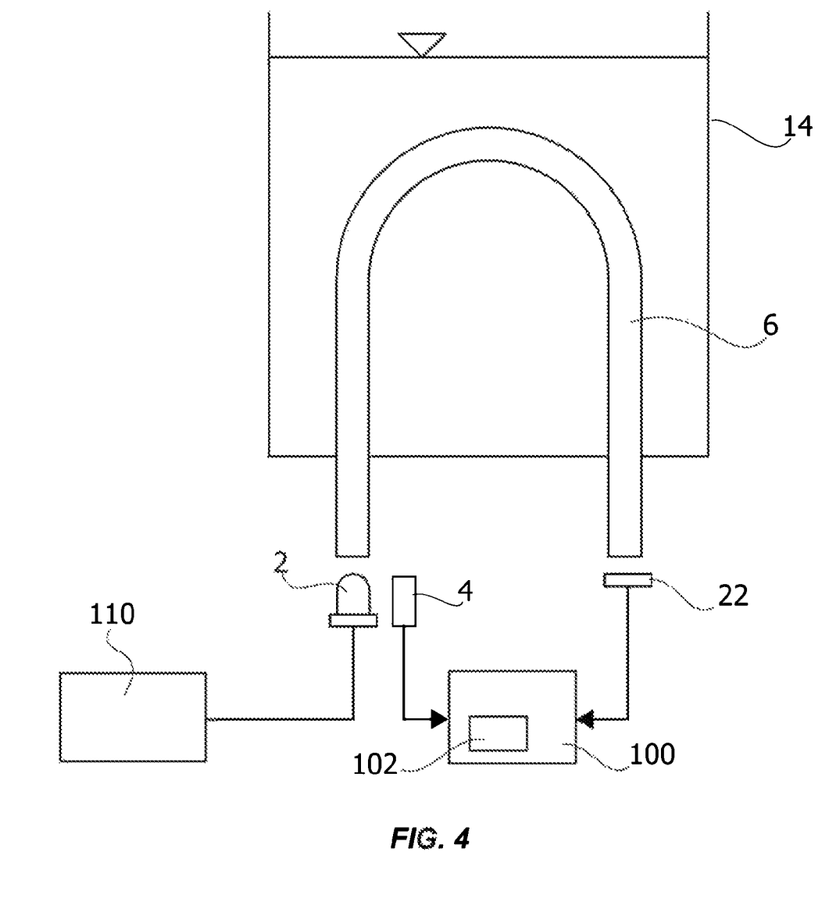
FIG. 4 is a schematic illustration of the device of FIG. 1 including the control means with which it is equipped.

In various embodiments, as in the one illustrated in FIGS. 1 to 4, the sensor device, designated in the figures by the reference 10, comprises an emitter of light radiation 2, at least one means 4 for receiving light radiation, and a propagation medium or light guide 6 that optically connects the receiving means to the emitter. As will be seen in greater detail in what follows, the propagation medium is configured so as to present at least one surface that, during the operation of the device, remains immersed in the solution the concentration of which is to be measured. The interface of separation between the propagation medium and the solution, which is characterized by the refractive index of the propagation medium and the refractive index of the solution, determines—together with other parameters of the device—the amount of light radiation that traverses the propagation medium and the amount of radiation that is, instead, dispersed within the solution. FIG. 4 illustrates schematically the configuration of the device described herein.

It is now to be noted that the present applicant has found that, at least within a range of concentration of urea in water comprised between 0% and 50%, within which the conditions of use of the sensor device described herein certainly fall, the value of the refractive index of the solution of urea in water depends linearly upon the value of the concentration of urea in the solution. It follows that the value of the concentration of urea can be derived directly from the value of the refractive index of the solution.

In the framework of the device described herein, the refractive index of the solution is correlated to the loss of intensity of radiation due to the interface of separation between the propagation medium and the solution. This loss can be calculated on the basis of the value of intensity detected by the receiving means. Consequently, the value of concentration of urea in the solution being measured can be derived as a function of the value of intensity detected by the receiving means. In the light of the foregoing, the device described herein thus comprises control means 100 configured for obtaining a value indicating the concentration of urea as a function of the signal coming from the receiving means.

In various embodiments, the control unit is configured for obtaining a value indicating the aforesaid loss of intensity on the basis of the signal coming from the receiving means. In various embodiments, as in the one illustrated, the control means comprise a computing module 102 designed to determine the value of the concentration of urea starting from the value of the loss of intensity, through a mathematical function derived experimentally. In various embodiments, the control unit comprises a storage module containing one or more maps, which are also derived experimentally, representing matching between values of loss of intensity and values of concentration of urea, and the control unit is configured for obtaining, on the basis of the aforesaid maps, the concentration value corresponding to the given value of loss of intensity.

The aforesaid function or the aforesaid maps set in correlation the value of loss of intensity that takes place in the propagation medium with the value of the concentration of urea in the solution measured. Preferably, they are obtained experimentally during a process of calibration of the device.

According to a preferred embodiment, the calibration process envisages, as first step, obtaining the value of loss of intensity of radiation through the propagation medium in a condition where the latter is air. This enables determination of the losses intrinsic to the device, namely, the losses that are basically due to the geometry of the optical fibre and to the various parameters directly connected thereto. Next, the process envisages obtaining the value of loss of intensity with the propagation medium immersed in the solution, for a series of conditions that differ from one another as regards the value of concentration of urea in the solution (for example, for concentrations of 0%, 32.5% and 50%, respectively). On the basis of the data gathered it is possible to derive the experimental law, i.e., the function that, in the specific device being calibrated, links the loss of intensity measured to the concentration of urea in the solution. It should be noted that, in the example of embodiment illustrated, this law is of a linear type. As has been seen above, the control unit uses the function obtained in the way described and/or the corresponding maps of values to obtain the value of concentration of urea corresponding to the value of loss of intensity obtained on the basis of the signal received by the receiving means. As mentioned at the start, the concentration value derived is used at input by the control unit of the catalytic system for calibrating the operating mode of the system.

In various preferred embodiments, as in the one illustrated, the control unit is moreover configured for comparing the concentration value found with a maximum reference value and a minimum reference value and for identifying a state of alert in the case where the value found falls outside the range defined by the two reference values.

It is clear that, to determine the value of concentration of urea, the control means can also use a value of intensity directly derived from the signal coming from the receiving means, without obtaining the losses of intensity that occur in the propagation medium, considering this value of intensity as an indirect indication of the above losses; to do this, clearly it is assumed that the intensity of the radiation emitted by the emitter remains constant in time, or else means are implemented designed to keep the intensity effectively constant.

As emerges from the foregoing, the device described herein is thus able to determine the concentration of urea in water and is moreover able to verify whether this is within the expected operating range referred to at the start of the present description.

Furthermore, in order to be able to signal the presence of contaminants, in particular non-mixable contaminants, in the solution being measured, the control means of the device can also be configured so as to be able to detect stable and sudden changes of the signal received by the receiving means, or in any case changes by a value processed by the control means on the basis of the aforesaid signal, that represent a sharp and non-gradual variation of the loss of intensity of light that occurs in the fibre owing to the fact that the optical fibre has been in fact covered by the contaminant (thus modifying the optical characteristics of the interface of separation between the fibre and the solution). The control means are moreover configured for indicating a state of alert as a consequence of the aforesaid detection.

It is now to be noted that the present applicant has also found that, in the framework of the device as described above, the losses of intensity of radiation in three different ranges of wavelength all follow a respective law of variation as the concentration of urea varies. The set of the aforesaid laws or functions is specific for the solution of urea and water in question for the ranges of wavelength considered and thus constitutes a sort of fingerprint of the solution.

Figure 5:
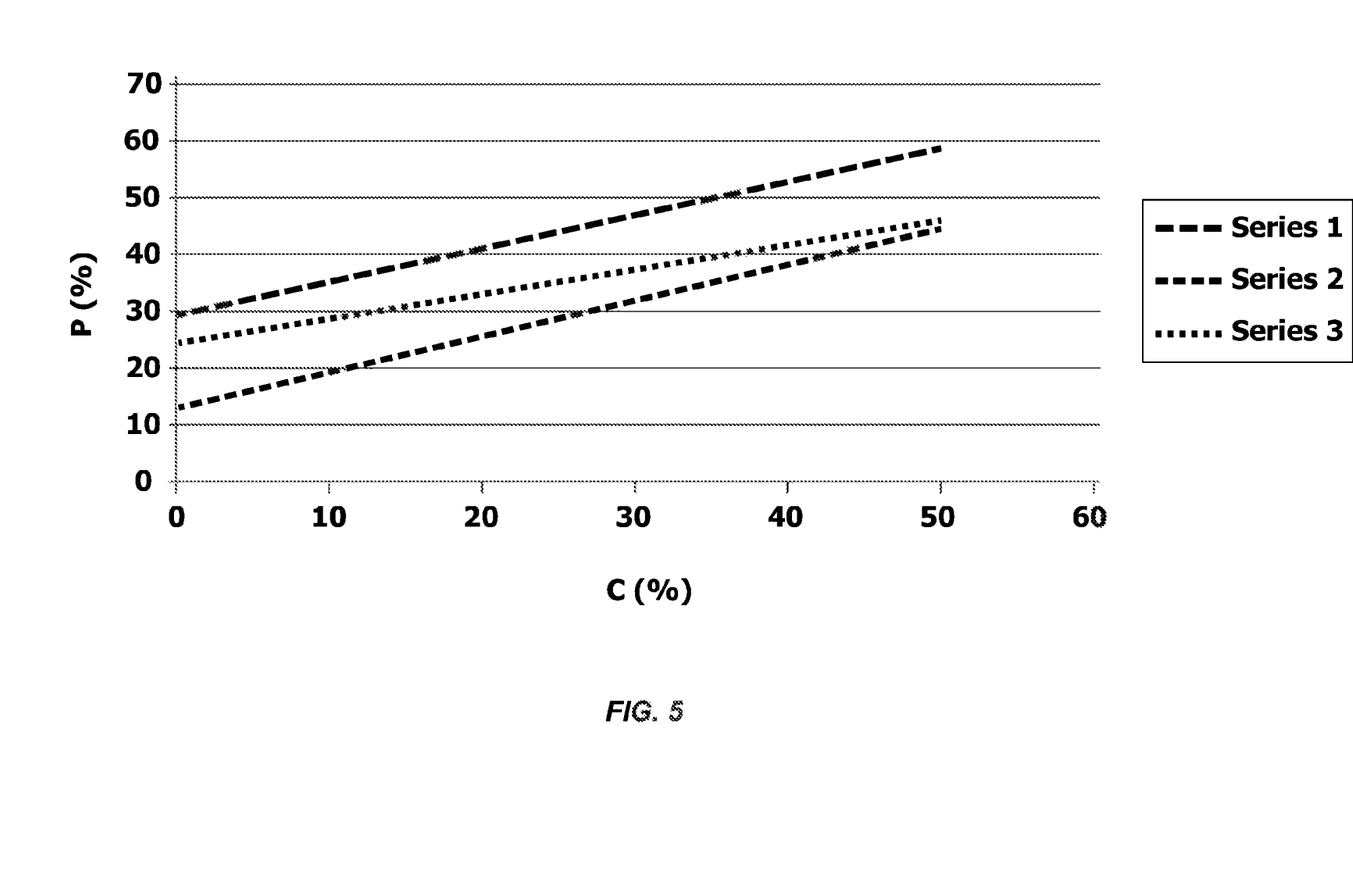
FIG. 5 is a characteristic diagram of a solution of urea and water, obtained experimentally, that plots the losses of intensity of radiation in the device described herein as the concentration of urea varies.

In this connection, FIG. 5 illustrates a diagram, appearing on the abscissae of which are the values of concentration of urea C (expressed in weight percent) and on the ordinates of which are values of loss of intensity P; the loss of intensity represented is expressed in percentage and refers to the loss that can be put down to the interface of separation discussed above, in the presence of a solution containing a concentration of urea ranging from 0% to 50%. The three straight lines represent the plot of the losses of intensity in the light guide as a function of the variation of the concentration of urea in the red (Series 1), in the green (Series 2), and in the blue (Series 3).

Among other things, as emerges from the above diagram, the losses in the three different ranges of wavelength is keep in a ratio substantially constant as the concentration of urea in water varies.

Diagrams of this type have been obtained also for combinations of ranges of wavelength different from the red, blue, and green series.

The present applicant has hence considered exploiting the above finding in order to determine a control method via which to verify that the solution undergoing measurement is precisely the solution of urea and water expected.

For this purpose, in various embodiments, as in the one illustrated, the emitting means is configured for emitting radiation in at least three different ranges of wavelength, and the receiving means is configured for detecting radiation in the same three ranges.

The control means are configured for obtaining, for a first one of the ranges of wavelength, the value of the concentration of urea with the modalities described previously, applying the specific function of the solution for the aforesaid first range.

The control means are moreover configured for processing the signals coming from the receiving means for the other two ranges of wavelength, and for verifying whether corresponding values of these signals satisfy, together with the value of concentration of urea previously found, the two characteristic functions of the solution for the other two ranges of wavelength.

In various preferred embodiments, as in the one illustrated, the control means are configured for obtaining values indicating the losses of intensity of radiation in the three different ranges of wavelength and for deriving, for a first one of the ranges of wavelength, the value of the concentration of urea in the modalities described previously, applying the characteristic function of the solution for this first range. The control means further comprise a comparison module, designed to verify whether the values indicating the losses of intensity for the other two ranges of wavelength, together with the value of concentration of urea previously derived, satisfy the two functions of the solution for the other two ranges of wavelength.

In various embodiments, the control means are configured for indicating a state of alarm in the case where the given functions are not satisfied. By so doing, the device is thus able to detect the presence of foreign liquids. In the context of these verifications, the control means can clearly use tolerance thresholds.

Also in this case, it is clear that the control means can also use values of intensity directly derived from the signals coming from the receiving means, without obtaining the losses of intensity that occur in the propagation medium.

Figure 6:
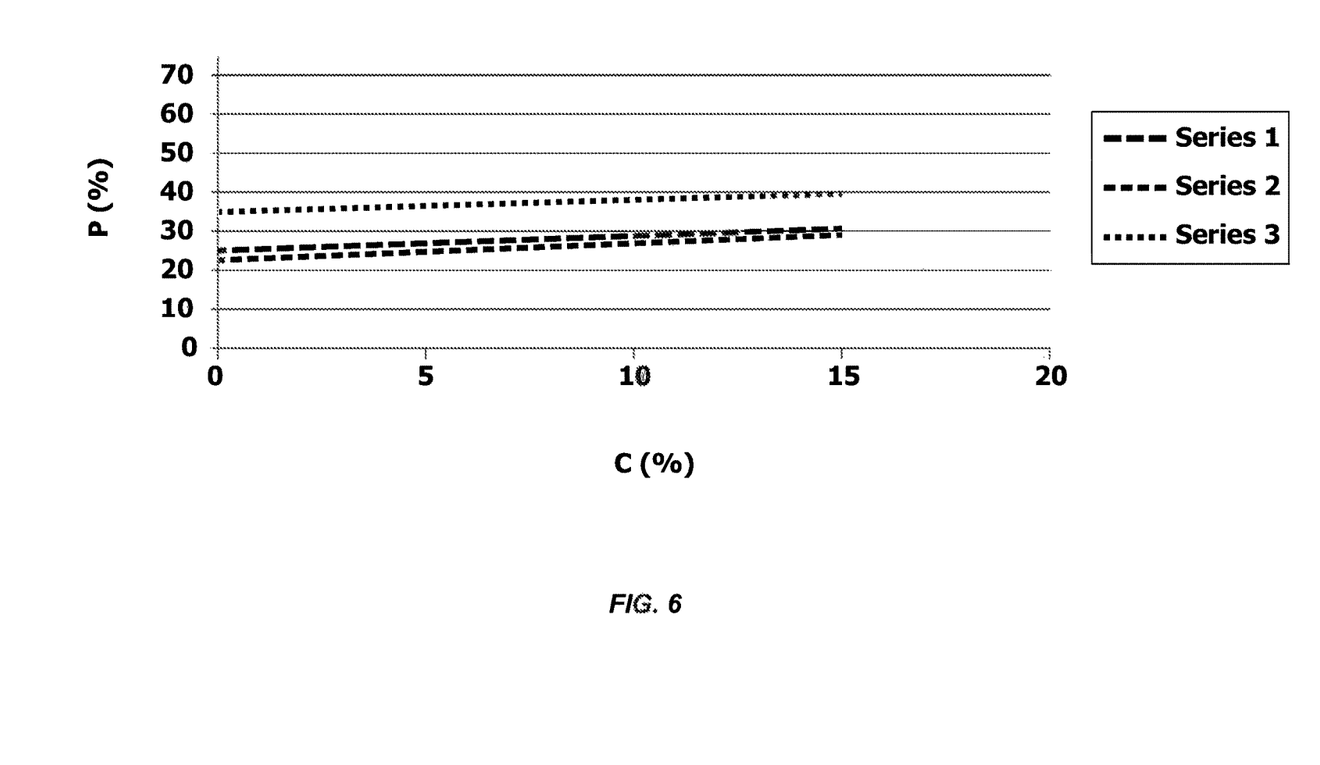
FIG. 6 is a diagram similar to that of FIG. 5 for a solution of water and sodium chloride.

It should now be noted that FIG. 6 represents a diagram similar to that of FIG. 5, for a solution of water and sodium chloride. As is evident from this diagram, also for a solution of water and sodium chloride the losses of intensity of the radiation in the three ranges examined, red, blue, and green, exhibit a reciprocal ratio that remains substantially constant and that is characteristic of the type of solution. This ratio differs clearly from the one for the solution of urea and water.

The present applicant has obtained the same type of diagram for other types of solutions in water, for example solutions of ethylene glycol, ethanol, acetic acid, methanol, etc., and for all of these a ratio between losses of intensity has been identified in the three ranges examined, which is specific for the type of solution.

This shows that the device described herein can be effectively used also in applications different from the one discussed herein.

It is to be noted that the present applicant has found that the same control method as the one discussed above could be implemented also with reference to just two different ranges of wavelength as well as to a number of ranges greater than three.

Figure 1:
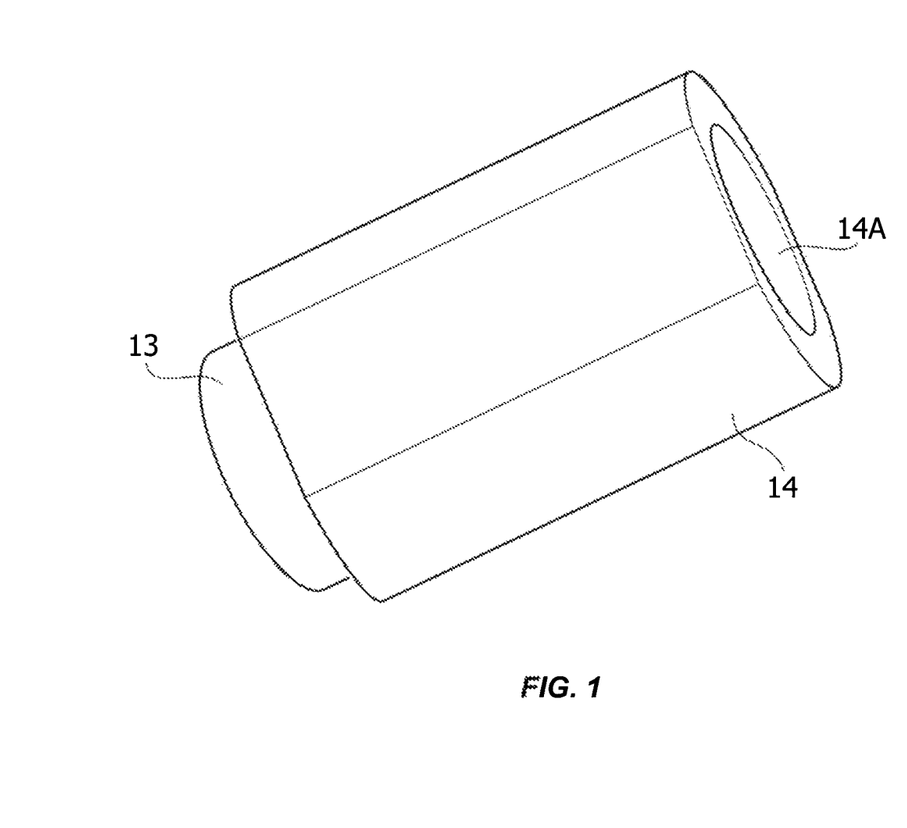
FIG. 1 is a perspective view of an embodiment of the device described herein.

With reference now to FIGS. 1 to 3, in various embodiments, as in the ones illustrated in FIGS. 2 and 3, the propagation medium 6 is constituted by an optical fibre that follows a development that for at least one portion has a given variation of direction, this variation in itself being constant or variable, in order to concentrate in this portion the losses of intensity of the radiation that traverses the propagation medium. In various preferred embodiments, as in the one illustrated in FIGS. 1 to 3, the propagation medium 6 has a generic U-shaped development.

The device comprises a base element 12, having a cylindrical geometry, which has respective openings 12A, 12B in directions parallel to the axial direction of the base body, that are to receive the two rectilinear end portions of the optical fibre. A plate 16 having corresponding openings 16A, 16B is coupled to the body 12, via interposition of gaskets 17 positioned at the openings 12A, 12B and 16A, 16B, so that the rectilinear portions of the optical fibre received in the body 12 are isolated from the solution of urea and water.

The fibre projects from the set of the base body 12 and of the plate 16, with its elbow-shaped portion and, possibly, with rectilinear portions constituting the prolongation of the end portions housed in the base body so that it can be immersed in the solution of urea and water. In various embodiments, as in the ones illustrated in FIGS. 2 and 3, the base body has, on the side opposite to the one from which the optical fibre projects, a first seat 12C (visible in FIG. 2), giving out into one of the two openings of the base body, that is designed to receive the emitter 2, and a second seat 12D (which is also visible in FIG. 2), giving out into the other opening of the base body, that is designed to receive the receiving means 4.

In various preferred embodiments, as in the ones illustrated in FIGS. 2 and 3, the emitter is a LED source, preferably governed by a driving module 110 configured for supplying the source with an appropriate current signal. In the embodiment in which the device is prearranged for operating with radiation in three different ranges of wavelength, the aforesaid source preferably comprises three LEDs designed to emit light of different colours, for example red, green, and blue. In various embodiments, as in the ones illustrated, the receiving means is a photoelectric detector, for example a photodiode, suited to detecting radiation in the range or in the ranges of wavelength in which the emitter operates. In the embodiments in which the device operates in three ranges of wavelength, the receiving means is preferably a photoelectric sensor with three bands of wavelength, for example of the RGB type.

The device described herein further comprises a protective casing 14 coupled, via interposition of a gasket 15, to the base body 12, configured for protecting from impact the portion of the optical fibre that projects from the base body. The casing has, at the top, a top opening 14A, through which it can be filled with the solution to be measured so that the optical fibre will be completely submerged thereby.

The casing 14 has inside an annular surface 14' facing the end of the casing opposite to the one having the opening 14A, against which the gasket 15 and the ensemble of the body 12 and of the plate 16 are packed by a body 13 for closing the device, which is screwed into the casing 14.

In various embodiments, as in the ones illustrated, the device described herein further comprises a second receiving means 22, which is prearranged for detecting a value indicating the intensity of the radiation emitted by the emitter, before this is channelled along the optical fibre 6. In various embodiments, as in the one illustrated, the receiving means in question is set immediately adjacent to the emitter so as to be able to receive directly part of the radiation emitted by the latter. In various preferred embodiments, as in the one illustrated in FIG. 2, for this purpose the seat 12C is prearranged for receiving together the emitter and the second receiving means. In various alternative embodiments, as in the one illustrated in FIG. 3, the second receiving means 22 is instead set at a distance from the emitter, within a further seat 12E made in the base body 12 on the same side in which the seats 12C and 12D are provided, and is connected to the base body 12 via a further optical fibre 24 completely contained in the body 12. The embodiments of FIGS. 2 and 3 are hence basically distinguished by the presence of the further optical fibre 24 in the embodiment of FIG. 3.

As compared to the case where the emitter is constituted by a LED source, it is to be noted that the LEDs are characterized by the presence, in addition to the main emission beam, of a secondary side beam, which generally is never exploited for the purposes of lighting.

On the basis of what has been described above, in the framework of the device described herein, instead, the aforesaid secondary beam is used for obtaining, precisely, the value of the intensity of the radiation emitted by the source. The present applicant has in this connection found that there exists a ratio K between the intensity of the main beam and the intensity of the secondary beam. On the basis of this ratio, by identifying the intensity of the secondary beam, it is thus possible to obtain the intensity of the main beam.

In various embodiments, as in the one illustrated, the control means of the device are thus configured for multiplying by the factor K the intensity detected by the second receiving means and using the value thus obtained as reference value, starting from which the losses of intensity may be calculated on the basis of the intensity detected by the first receiving means.

The check made via the second receiving means enables the variations of luminance by the emitter due to external parameters, such as for example temperature, or else due to ageing of the emitter, to be taken into account so that the device will be able to guarantee precise and reliable detection throughout its life cycle.

Of course, without prejudice to the principle of the invention, the details of construction and the embodiments may vary, even significantly, with respect to what has been illustrated herein purely by way of non-limiting example, without thereby departing from the scope of the invention, as defined by the annexed claims.

The invention claimed is:

1. A device for detecting the concentration of urea in solution with water, comprising:
  a means for emitting radiation;
  at least one means for receiving radiation, which is configured for detecting a value of intensity of radiation;
  a light guide, which is prearranged for optically connecting said emitting means to said receiving means, wherein said light guide has at least one surface that is to come into contact with said solution so as to determine an interface of separation between said light guide and said solution,
  control means configured for obtaining a value indicating the concentration of urea in said solution as a function of the signal coming from said receiving means;
  said light guide having a general U-shaped development and the elbow-shaped portion of said guide defining at least part of said surface that is to come into contact with said solution;
  said emitting means configured for emitting radiation in at least one first range of wavelengths and one second range of wavelengths that are different and said receiving means is configured for detecting radiation in the said first range and said second range;
  said control means configured for obtaining a value indicating the concentration of urea in said solution as a function of a first signal coming from said receiving means, for said first range of wavelengths, and for verifying whether said value indicating concentration and a value of intensity of radiation derived from a second signal coming from said receiving means, for said second range of wavelengths, satisfy a given function, characteristic of said solution, for said second range of wavelengths.

2. The device according to claim 1, wherein said receiving means is configured for detecting a value of intensity of radiation.

3. The device according to claim 1, wherein said control means are configured for processing a value indicating the intensity of radiation derived from the signal coming from said receiving means so as to obtain said value indicating concentration.

4. The device according to claim 1, wherein said control means are configured for obtaining a value indicating the loss of intensity of the radiation that traverses said light guide on the basis of the signal coming from said receiving means (4).

5. The device according to claim 1, wherein said control means comprise a computing module designed to determine, through a mathematical function derived experimentally, said value indicating the concentration of said element, starting from a value of intensity of radiation derived from the signal received by said receiving means, and/or wherein said control unit comprises a storage module containing one or more maps derived experimentally, which represent matching between values of concentration and values of intensity of radiation, and wherein the control unit is configured for obtaining via said maps said value indicating concentration on the basis of a value of intensity of radiation derived from the signal received by said receiving means.

6. The device according to claim 1, comprising a second means for receiving radiation, which is prearranged for detecting radiation emitted by said emitter that does not propagate in said light guide.

7. The device according to claim 6, wherein said second receiving means is prearranged for detecting values of intensity of radiation, and wherein said control means are configured for determining a value indicating the intensity of the radiation emitted by said emitter that are channelled along said light guide, as a function of the signal received by said second receiving means.

8. The device according to claim 7, wherein said receiving means is a first receiving means and is configured for detecting a value of intensity of radiation, and wherein said control means are configured for obtaining a value indicating the loss of intensity of the radiation that traverses said light guide on the basis of the signals coming from said first and second receiving means.

9. The device according to claim 1, wherein said control means comprise a comparison module designed to verify whether a value indicating intensity of radiation derived from said second signal coming from said receiving means, together with said value indicating concentration, satisfy said characteristic function of said solution.

10. A method for detecting the concentration of urea within a solution of urea and water, comprising the steps of:
  providing a means for emitting radiation, at least one means for receiving radiation, and a light guide, which is prearranged for optically connecting said emitting means to said receiving means, wherein said light guide has at least one surface that is to come into contact with said solution so as to determine an interface of separation between said light guide and said solution,
emitting radiation from said means for emitting radiation and obtaining a signal from said receiving means,
obtaining a value indicating the concentration of urea in said solution as a function of the signal coming from said receiving means;
wherein said light guide comprises a general U-shaped development and an elbow-shaped portion of said guide defines at least part of said surface that is to come into contact with said solution, wherein the providing said emitting means and said receiving means include, respectively, providing an emitting means configured for emitting radiation in at least one first range of wavelengths and one second range of wavelengths that are different, and providing a receiving means configured for detecting radiation in said first and second ranges;
obtaining a value indicating the concentration of urea in said solution as a function of a first signal coming from said receiving means, for said first range of wavelengths;
providing a value of intensity of radiation derived from a second signal coming from said receiving means, for said second range of wavelengths; and
verifying whether said value indicating concentration and said value of intensity of radiation satisfy a given characteristic function of said solution for said second range of wavelengths.

11. The method according to claim 10, comprising the step of determining, through a mathematical function derived experimentally, said value indicating the concentration of urea starting from a value of intensity of radiation derived from the signal received by said receiving means, and/or providing one or more maps derived experimentally, representing matching between values of concentration and values of intensity of radiation, and obtaining, via said maps, said value indicating concentration on the basis of a value of intensity of radiation derived from the signal coming from said receiving means.

12. The method according to claim 10, comprising the steps of:
providing an emitting means configured for emitting radiation in at least one first range of wavelengths and one second range of wavelengths that are different and a receiving means configured for detecting radiation in the same ranges;
obtaining a value indicating the concentration of urea in said solution as a function of a first signal coming from said receiving means, for said first range of wavelengths;
providing a value of intensity of radiation derived from a second signal coming from said receiving means, for said second range of wavelengths; and
verifying whether said value indicating concentration and said value of intensity of radiation satisfy a given characteristic function of said solution for said second range of wavelengths.

13. The method according to claim 11, comprising the steps of:
providing an emitting means configured for emitting radiation in at least one first range of wavelengths and one second range of wavelengths that are different and a receiving means configured for detecting radiation in the same ranges;
obtaining a value indicating the concentration of urea in said solution as a function of a first signal coming from said receiving means, for said first range of wavelengths;
providing a value of intensity of radiation derived from a second signal coming from said receiving means, for said second range of wavelengths; and
verifying whether said value indicating concentration and said value of intensity of radiation satisfy a given characteristic function of said solution for said second range of wavelengths.

* * * * *